United States Patent [19]

Goins et al.

[11] Patent Number: 4,631,349

[45] Date of Patent: * Dec. 23, 1986

[54] HETEROGENEOUS CATALYST PROCESS

[75] Inventors: Dixie E. Goins, Orangeburg; Silas W. Holmes, Columbia; Edward A. Burt, Orangeburg, all of S.C.

[73] Assignee: Ethyl Corporation, Richmond, Va.

[*] Notice: The portion of the term of this patent subsequent to Dec. 9, 2003 has been disclaimed.

[21] Appl. No.: 748,733

[22] Filed: Jun. 25, 1985

[51] Int. Cl.$^4$ .............................................. C07C 37/14
[52] U.S. Cl. ................................ 568/789; 568/780; 568/784; 568/785
[58] Field of Search ............... 568/789, 785, 784, 780, 568/781, 783, 788, 794; 502/159

[56] References Cited

U.S. PATENT DOCUMENTS

| | | | |
|---|---|---|---|
| 2,442,878 | 6/1948 | Schmerling et al. | 568/794 |
| 2,831,898 | 4/1958 | Ecke | 568/789 |
| 3,091,646 | 5/1963 | Leston | 568/784 |
| 3,290,389 | 12/1966 | Hahn | 568/794 |
| 3,355,504 | 11/1967 | Coffield et al. | 568/794 |
| 3,422,157 | 1/1969 | Kaufman et al. | 568/784 |
| 3,426,358 | 2/1969 | Schlichting et al. | 568/794 |
| 3,798,281 | 3/1974 | Wang | 502/159 |
| 3,843,606 | 10/1974 | Von Srge | 568/804 |
| 3,933,927 | 1/1976 | Goddard | 568/784 |
| 4,113,976 | 9/1978 | Michurov et al. | 568/789 |
| 4,398,048 | 8/1983 | Firth | 568/790 |
| 4,461,916 | 7/1984 | Alfs | 568/785 |
| 4,476,329 | 10/1984 | Chambers et al. | 568/780 |

FOREIGN PATENT DOCUMENTS

| | | | |
|---|---|---|---|
| 59-130823 | 6/1984 | Japan | 568/794 |
| 455742 | 1/1975 | U.S.S.R. | 502/159 |
| 0789483 | 12/1980 | U.S.S.R. | 568/804 |

*Primary Examiner*—Werren B. Lone
*Attorney, Agent, or Firm*—Donald L. Johnson; John F. Sieberth; Edward F. Sherer

[57] ABSTRACT

A process using heterogeneous resin-bonded aluminum phenoxide catalyst to alkylate phenols, the catalyst per se, and a process for making the catalyst. The inventive alkylation process uses ortho-tert-butylphenoxide bonded to a phenolformaldehyde condensation resin heterogeneous catalyst to prepare 2,6-di-tert-butyl-phenol from isobutylene and ortho-tert-butylphenol.

41 Claims, No Drawings

HETEROGENEOUS CATALYST PROCESS

BACKGROUND OF THE INVENTION

1. Field of the Invention

This invention relates to heterogeneous catalysts and processes using such catalysts for the alkylation of phenols. More particularly, this invention relates to the preparation of ortho-alkylphenols in high purity with a minimum of impurity by-products.

CROSS-REFERENCE

This application is related to copending application Ser. No. 748,744 filed June 25, 1985, commonly assigned.

2. Description of the Prior Art

The alkylation of phenols has been carried out using homogeneous aluminum phenoxide catalysts in a pressurized liquid/gas reaction to prepare ortho-alkylphenols. However, such processes commonly produce significant amounts of 2,4-dialkylphenols or 2,4,6-trialkylphenols and suffer from other problems. In particular, current homogeneously catalyzed alkylations have waste problems and require acidification and neutralization steps which increase the overall cost of the process.

U.S. Pat. No. 3,355,504 describes the "ortho catalyst" used for the conversion of an ortho-alkylphenol to a 2,6-dialkylphenol. The ortho catalyst is an aluminum 2-substituted phenoxide which strongly directs the production of 2,6-dialkylphenols rather than the 2,4,6-trialkylphenol. The "ortho catalyst" must be used in the substantial absence of phenol which does not have ortho substituents and ethers such as phenyl butylether which may generate phenol. This is because the phenol tends to replace the ortho-substituted phenol moiety on the aluminum 2-substituted phenoxide catalyst thereby destroying the strong alkylation directing effects.

The process described in U.S. Pat. No. 3,355,504 and other related processes use a homogeneous aluminum phenoxide catalyst which, after alkylation with, e.g., isobutylene, must be acidified for a phase cut followed by neutralization with sodium carbonate so as to avoid corrosion of distillation columns and also avoid dealkylation of product in the columns which are operated at temperatures that might otherwise favor dealkylation. Thereafter, the aqueous phase of the mixture is sent to a caustic solution for precipitation of an aluminum salt which is contaminated with phenol. This presents an immense disposal problem since the aluminum cannot otherwise be used or recovered. In the past, this aluminum precipitate has been disposed of as a phenol-bearing waste stream.

U.S. Pat. No. 3,652,685 describes the separation of aluminum catalyst materials which generate phenol-bearing aluminum waste.

SUMMARY OF THE INVENTION

The process of the present invention overcomes the disadvantages associated with separation procedures and greatly diminishes the costs of disposing of such waste. The invention is directed to an economical process for alkylating phenols, a new catalyst for the process, and a method of preparing the catalyst.

The present invention is a process for alkylating phenols comprising reacting a mixture of:

(a) a phenol having at least one ortho or para position unsubstituted except for H;

(b) an olefin; and (c) a heterogeneous catalyst comprising an aluminum phenoxide bonded to a solid polymeric resin.

The present invention is also a process for preparing a resinous catalyst useful in the alkylation of phenols, said process comprising reacting or an aluminum compound with a solid polymeric resin to attach aluminum to said resin and thereafter reacting a phenol with the aluminum attached to said resin to form a resin-bonded aluminum phenoxide catalyst.

The present invention is also a resin-bonded aluminum phenoxide catalyst of the formula:

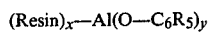

$$(Resin)_x-Al(O-C_6R_5)_y$$

wherein
x is 1 or 2;
y is 1, 2, or 3;
x+y is 3 or 4;
$C_6R_5$ is aromatic wherein the R are independently selected from H, alkyl of from 1 to 12 carbon atoms, cycloalkyl of from 5-12 carbon atoms, and aralkyl of from 7-12 carbon atoms, and
the Resin is the residue from a solid polymeric resin.

DESCRIPTION OF THE PREFERRED EMBODIMENTS

A preferred embodiment of the invention is a process for alkylating phenols comprising reacting a mixture of (a) a phenol having at least one ortho or para position unsubstituted except for H; (b) an olefin; and (c) a heterogeneous catalyst comprising an aluminum phenoxide bonded to a solid polymeric resin. The process is applicable to a broad range of phenols. The terms "a phenol" and "phenols" are used in a generic sense to include all aromatic hydroxy compounds having at least one hydroxy group bonded to an aromatic ring. The phenols usable with the process are those having at least one ortho or para position open for substitution. These include the compound phenol ($C_6H_5OH$), ortho-cresol, para-cresol, 2,6-dimethylphenol, paraethylphenol, 4-phenylphenol, alpha-naphthol, β-naphthol, ortho-chlorophenol, 4-chlorophenol, 2,4-dichlorophenol, 2,4-dibromophenol, 4-bromophenol, hydroquinone, 4-methoxyphenol, ortho-ethoxyphenol, ortho-tert-butylphenol, ortho-sec-butylphenol, ortho-isopropylphenol, 2,4-di-tert-butylphenol, 2,4-di-sec-butylphenol, 2,6-di-sec-butylphenol, 2,6-di-tert-butylphenol, 2,4-di-tert-sec-butylphenol, ortho-amylphenol, 2-n-octylphenol, 2-(4'-do-decyl)phenol, 2-(2'-decyl)phenol, 2-tert-amylphenol, 2,4-di-n-octylphenol, 2,6-diethylphenol, 2,6-dibenzylphenol, ortho-benzylphenol, 2,4-dibenzylphenol, 2(3'-nonyl)phenol, 2(3'-undecyl)phenol, 2-n-hexylphenol, 2,6-di-n-hexylphenol, 2-cyclohexylphenol, 4-cyclopentylphenol, 2,6-dicyclopentylphenol, 2,6-diisopropylphenol, ortho-isopropylphenol, 2,4-diisopropylphenol, ortho-n-butylphenol, 2-n-butyl-6-cyclohexylphenol, 2-pentyl-4-tert-butylphenol, 2(2'-heptyl)phenol, ortho-phenylphenol, 2,4-diphenylphenol, 2-ethyl-4-benzylphenol, and the like. The phenols may optionally be meta-substituted.

The phenolic reactants of the invention may have an optional halo substituent. The halo may be, e.g. bromo or chloro.

A preferred class of phenols includes the compound phenol and various lower alkyl substituted phenols having at least one ortho position unsubstituted except for hydrogen such as ortho-tert-butylphenol, ortho-isopropylphenol, 2,4-di-tert-butylphenol, ortho-cresol, para-cresol, ortho-sec-butylphenol, and the like. Very highly preferred phenols usable with the invention are the compound phenol, ortho-tert-butylphenol, ortho-isopropylphenol, and ortho-sec-butylphenol.

The resin-bonded aluminum phenoxide heterogeneous catalyst of the invention is a stable aluminum complex. The complex is tricoordinated but is in some cases tetracoordinated. The degree of coordination depends on the resin used and especially on the phenoxide moiety of the catalyst. An unsubstituted phenoxide moiety tends to tetracoordinate more than a substituted phenoxide moiety.

The process of the invention is applicable to phenols having the structure:

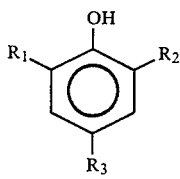

(I)

wherein $R_1$, $R_2$, and $R_3$ are independently selected from the group consisting of H, alkyl of from 1-12 carbon atoms, cycloalkyl of from 5-12 carbon atoms, and aralkyl of from 7-12 carbon atoms wherein at least one of $R_1$, $R_2$, and $R_3$ is H. In a preferred embodiment at least one of $R_1$ and $R_2$ is hydrogen. In a more preferred embodiment of the invention, $R_2$ and $R_3$ are both H and $R_1$ is alkyl of from 1-12 carbon atoms, more preferably sec-alkyl or tert-alkyl, still more preferably sec-butyl, isobutyl, or tert-butyl. Alternatively, $R_1$ may be methyl in still another embodiment of the invention. The phenols may optionally be meta-substituted.

In general, the heterogeneously catalyzed process of the present invention is usable with any of the various phenols which were heretofore catalyzed by homogeneous catalyst systems.

A process of the invention is preferably carried out in a liquid reaction medium. The medium may be an excess of one or both of the reactants or an innocuous liquid medium.

For alkylation processes using a heterogeneous "ortho" catalyst, the use of excess olefin (e.g., isobutylene) is highly preferred because this permits carrying out the process at a temperature below the melting point of the product 2,6-dialkylphenol. As the product is formed, it remains, however, dissolved in the excess olefin. Operation at the lower temperature advantageously decreases the amount of by-products and increases the yield based on ortho-alkylphenol.

In one embodiment, the liquid reaction medium is a hydrocarbon. Thus any of the well known hydrocarbon reaction mediums such as toluene, hexane, heptane, trimethylpentane, xylene, and the like are suitable for the invention, toluene being preferred.

In general, the olefins used in homogeneously catalyzed alkylation processes are also usable in the heterogeneously catalyzed alkylation process of the invention. The term "olefin" is meant to include monoolefinic alicyclic alkenes of from 2-12 carbon atoms, cycloalkenes of from 5-12 carbon atoms, and aralkenes of from 8-12 carbon atoms. That is, the olefins of the process of the invention are generally unsaturated compounds of the aliphatic, alicyclic, or araliphatic series with olefinic double bonds. Typical representatives of such compounds are those containing ethylenic unsaturation, such as ethylene, propylene, butylene, pentene, hexene, cyclopentene, cyclohexene, cyclooctene, styrene and α-methylstyrene including all possible isomers. It is particularly advantageous to use lower olefins such as those available from catalytic cracking processes, e.g. ethylene, propylene, amylene, and the isomeric butenes, such as 1- or 2-butene. In addition to the ethylenic unsaturated type compounds such as pent-1-ene, n-hex-1-ene, n-oct-1-ene, and the like, such alkenes substituted by methyl, ethyl, n-propyl, isopropyl, n-butyl, isobutyl, sec-butyl, or tert-butyl in the 2-, 3-, or 4-position are also usable. These include 2,3-dimethyl-n-butene, 3,3-dimethyl-n-butene, 2,5-dimethylheptene, 3,3-dimethylheptene, 2,3,4-trimethylheptene, 2,4-dimethylheptene, 2,3-dimethylheptene, 4,4-dimethylheptene, 2,3-diethylhexene, 2-methyl-3-ethylpentene, 2,4,4-trimethylpentene, 2,3,3,4-tetramethylpentene, and analagous alkenes wherein the double bond is in the 2-position or 3-position of the molecule. Also usable are the branched alkenes as obtained in the form of mixtures from the dimerization of isobutene or n-butene or the trimerizing of isobutene or n-butene or propene or by tetramerizing propene. Arylalkenes can be used such as styrene, alpha-methylstyrene, ortho-methylstyrene, meta-methylstyrene, para-methylstyrene, 3,4-dimethylstyrene, ortho-ethylstyrene, 3,4-diethylstyrene, ortho-propylstyrene, ortho-isobutylstyrene, ortho-tert-butylstyrene, and the like.

The catalyst materials of the invention are referred to as heterogeneous because they are solid in nature and do not usually dissolve in the otherwise homogeneous reaction mixture of a phenol and olefin (and liquid reaction medium such as toluene). Compare the homogeneously catalyzed processes wherein aluminum phenoxides are formed by the reaction of aluminum or aluminum alkyls with a phenol to form a catalyst which is generally readily dissolved in the reaction medium.

Therefore, in a batch operation it is generally preferred in the process of the invention to use agitation, preferably high speed sheer agitation to assure the distribution of the heterogeneous catalyst solid materials throughout the reaction mixture. Excess agitation which would destroy the structure or particle size of the heterogeneous catalyst is usually not helpful and is undesirable. Generally, any of the aluminum precursors and a phenol which was used to prepare a homogeneous catalyst heretofore used are also usable according to the present invention to prepare a heterogeneous catalyst for the process of the invention.

In most embodiments of the invention, it is generally preferred that the olefins and alkyl groups have at least 4 carbon atoms as the process is thereby accomplished more speedily. It is particularly preferred that isobutylene be used and that the mono-ortho-substituted phenol be 2-tert-butylphenol. The products achieved by using these materials are commercial antioxidants which have a strong demand in the market place. In general, in a preferred embodiment of the invention, the olefin corresponds to the alkyl substituent $R_1$ as given in structure I above thereby providing a more facile and speedier reaction. Thus the heterogeneous "ortho catalyst" is a particularly preferred embodiment of this invention.

The phenols usable to prepare the heterogeneous catalyst of the invention include any of the phenols mentioned above as reactant and, for purposes of preparing a heterogeneous "ortho catalyst", the ortho substituted phenols are preferred. Of course, the compound phenol, $C_6H_5OH$, usable as a reactant above, is also usable to prepare a heterogeneous catalyst of the invention wherein aluminum phenoxide is bonded through aluminum to a solid polymeric resin useful in the alkylation of phenols. In a highly preferred embodiment using the heterogeneous "ortho catalyst", the ortho alkyl substituent of the ortho-alkylphenol to be alkylated is the same as the alkyl substituent on the aluminum phenoxide portion of the heterogeneous ortho catalyst.

The quantity of catalyst to be used in the invention depends on the activity of the particular catalyst chosen, the nature of the underlying resin, and the particular alkylation procedure to be carried out. In general, a discontinuous/batch alkylation can suitable be carried out with a little as 0.1% by weight to as high as 30% by weight catalyst based on the weight of phenol to be alkylated. More preferably, a range of 0.5 to 10.0% by weight catalyst based on the weight of phenol is conveniently used. In a continuous (e.g. fixed bed) method of operation, a high quantity of catalyst may be desired wherein the catalyst weight range is from 0.02 to 10 parts by weight catalyst per part by weight of phenol per hour passed therethrough. More preferably, the range is about 0.4 to 1.0 parts by weight catalyst per 1.0 part by weight of phenol per hour passed through the catalyst.

The heterogeneous catalysts of the invention include the reaction products formed by first reacting an aluminum alkyl or other reactive aluminum compound with a solid polymeric resin to bond the aluminum to the resin followed by reaction with a phenol to form an aluminum phenoxide bonded to the solid polymeric resin. The reactive aluminum compounds usable for preparation of the heterogeneous aluminum phenoxide catalyst include aluminum phenoxides, aluminum halides, aluminum alkyls, and others. Aluminum alkyl compounds such as trimethylaluminum, triethylaluminum, tri-n-propyl-aluminum, diisobutylaluminum hydride, and triisobutylaluminum may be used. Also suitable are compounds such as diethylaluminum malonate, diethylaluminum hydride, diethylaluminum chloride, ethylaluminum dichloride, ethylaluminum sesquichloride, methylaluminum sesquichloride, alane, triphenylaluminum, and the like. Other aluminum source compounds are also usable to react with a resin thereby bonding the aluminum to the resin. For example, diphenoxy aluminum hydroxide is usable.

The aluminum compounds can be added directly to the reaction system containing the resin or may be added along with an inert solvent such as hexane, benzene, or toluene. The preferred aluminum alkyl for bonding aluminum to a solid polymeric resin, because of its high reactivity, is triethylaluminum.

The solid polymeric resins of the heterogeneous catalysts of the invention may be of the ion exchange type, the adsorber type, or another type. In the process of preparing the heterogeneous catalysts of the invention the resins are chemically reacted with aluminum compounds.

The solid polymeric resins usable in the heterogeneous catalysts of the invention in general include all resins which have functional groups with a highly electronegative atom with a donateable hydrogen atom or other leaving group which facilitates reaction of the resin with an aluminum compound (aluminum phenylate, aluminum alkyl, aluminum phenoxide, etc.). The resin usable for the heterogeneous catalyst of the invention include those with amine, thiol, carboxylic acid, sulfonic acid, hydroxy, phenol, and other functionalities as well as hybrid resins with mixed functional groups. Furthermore, the resins may be matrix-modified by chlorination, nitration, amination, alkylation, or other modification of the resin matrix.

The various solid polymeric ion exchange, adsorbant, and other resins of the invention may be described in many fashions and are well known in other arts for their adsorption and ion exchange capabilities.

Solid polymeric resins usable with the invention include phenol-formaldehyde condensation resins having a hydroxyl functional group such as Rohm & Haas Duolite ® S-761 resin support; phenolic/amine resins having hydroxyl and amine functional groups such as Rohm & Hass Duolite ® S-587 support; mixed amine resins having amino, dialkylamine, etc. functional groups such as Rohm & Haas Duolite ® A-7 support; sulfonic acid resins having $SO_3H$ functional groups such as Rohm & Haas Amberlyst ® 15 resin or Dow Chemical Company Dowex ® MSC-1 resin; acrylic ester resins having the functional group—R-COOR—such as Rohm & Haas XAD-7 resin or Rohm & Haas XAD-8 resin; sulfoxide resins having the functional group—RCOORSOR—such as Rohm & Haas XAD-9 resin; amide ion exchange resins having the functional group—RCONHR—such as Rohm & Haas XAD-11 resin; phenolic/carboxlic resins having hydroxyl and carboxylic (COOH) functional groups such as Rohm & Haas Duolite ® CS-100 resin; thiol resins having the functional group —SH such as Sybron Corporation AG-52-88B resin; or carboxylic acid resins having the functional group —COOH such as Dow Chemical Company Dowex ® NWC-1 resin.

The cross-linked phenol-formaldehyde condensation resin of a preferred embodiment of the invention is in the form of moist granules having a particle size of about 0.3 to 1.2 mm with a moisture retention capacity of about 51–56%. Preferably, the resin is dried under vacuum at about 80° C. until substantially all the absorbed water which it normally retains has been removed. This particular resin is not always stable above 80° C. The resin has a typical surface area of about 200–300 square meters per gram and a pore volume of about 0.45 to 0.55 cubic centimeters per gram. The specific gravity of the resin is 1.11.

A generalized structure of a typical unit of Rohm & Haas Amberlite XAD-8 is given below:

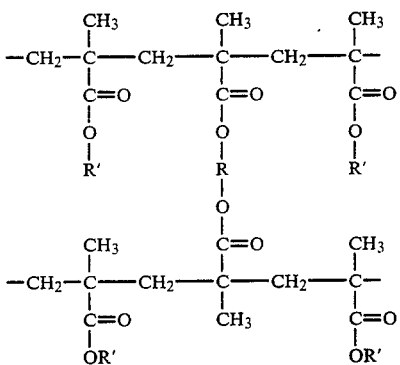

The Rohm & Haas Amberlite XAD-9 resin has the following substantial recurring structure:

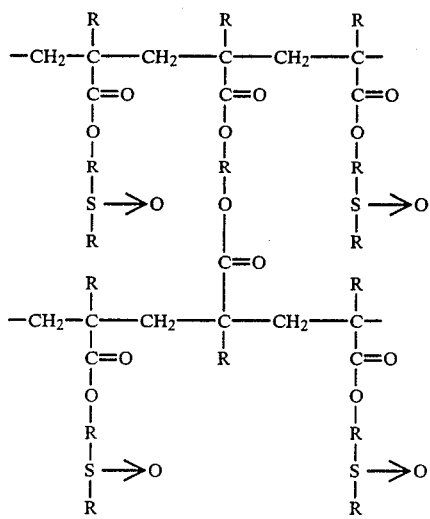

The use of the above described resins to form a heterogeneous catalyst for alkylation of phenols is highly desirable so as to provide an easily separable catalyst from the liquid reaction mixture containing alkylated product thereby avoiding the expensive hydrolysis procedure used with homogeneous catalyst systems. Thus, aluminum phenoxides including the "ortho catalyst" type of aluminum phenoxide can be chemically bonded to solid polymeric resins and used as a heterogeneous catalyst in the reaction of phenols and olefins. The catalyst life and the rate of aluminum loss varies depending upon the particular resin and the reaction conditions.

The yields for the processes using the heterogeneous catalysts of the invention are very similar to those observed for the homogeneous route but the process is, overall, much more economical. The heterogeneous reactions are sometimes slightly lower than the rates for homogeneous reactions with equivalent amounts of aluminum. However, this does not seriously detract from the significant savings available by the decrease in phenol-contaminated aluminum waste.

The present heterogeneously catalyzed process of the invention provides as much as a ten-fold decrease in the amount of aluminum waste stream and greatly reduces the distillation and energy requirements by improving conversions per pass. The phenol-formaldehyde condensation resin and cross-linked acrylic polyester resins are preferred for some embodiments of the invention including the heterogeneous "ortho catalyst".

In each homogeneously catalyzed alkylation of a phenol the amount of aluminum used as catalyst and lost is about 0.48 weight percent of the total reaction mixture or about 0.71 weight percent of the 2,6-dialkylphenol product. In experiments using the heterogeneous catalysts of the invention, as much as about 0.45 weight percent of the aluminum may be lost in a first heterogeneously catalyzed alkylation, but the rate of loss drops off precipitously (to nil) in subsequent alkylations recycling the same aluminum/resin heterogeneous catalyst while the catalyst remains active.

In a preferred embodiment of the present invention, an ortho-alkylphenol is first prepared by the olefin (e.g. isobutene, butene-1, etc.) alkylation of phenol using an aluminum-containing catalyst such as gamma alumina. Thereafter excess phenol or phenol generating ethers such as phenyl tert-butylether are removed from the ortho-alkylphenol (preferably ortho-tert-butylphenol) to obtain a substantially pure ortho-alkylphenol which is subsequently alkylated in a heterogeneous catalyst system using e.g. a phenol formaldehyde resin such as Duolite ® S-761 ion exchange resin. The absence of phenol and phenol-generating ethers is well recognized as a requirement for the homogeneous ortho catalyst and is equally applicable here for the heterogeneous ortho catalyst since the compound phenol $C_6H_5OH$ tends to replace the ortho catalyst material and thereby decrease the ortho influencing effect of the ortho catalyst material resulting in an increase of para-substitution products.

Advantageously, the process of the invention may be carried out wherein the heterogeneous catalyst of the invention is positioned in a fixed bed of sufficient size to provide conversion of the ortho alkylphenol (preferably ortho-tert-butylphenol or ortho-sec-butylphenol) reactant to 2,6-dialkylphenol with a very low production of 2,4,6-trialkylphenol and 2,4-dialkylphenol. Preferably, the same olefin is used in both stages of the preparation of the 2,6-dialkylphenol. For example, a preferred embodiment is the mono-ortho-alkylation of phenol with a gamma alumina catalyst using isobutylene followed by distillation to remove any remaining phenol and phenol-generating ethers in turn followed by the alkylation of the ortho-tert-butylphenol with isobutylene in the presence of the heterogeneous resin-bonded aluminum phenoxide catalyst wherein the phenoxide portion of the catalyst is ortho-tert-butylphenoxide.

According to the invention a reactive aluminum compound as previously described is reacted with a solid polymeric resin to attach or bond aluminum to the resin. For example, triethylaluminum may be added to a phenol-formaldehyde condensation resin thereby attaching the aluminum to the oxygen of the phenolic group which is pendant on the resin. This evolves ethane for each hydrogen removed from the pendant phenolic group of the resin. Alternatively, the triethylaluminum may bond with two adjacent pendant phenolic groups of the resin to evolve two moles of ethane, one for each hydrogen atom extracted from the hydroxyl of the pendant phenol groups. This leaves the aluminum twice bonded to the resin with one remaining pendant reactive ethyl substituent on the aluminum.

Typically, excess triethylaluminum or similar aluminum alkyl is removed by full toluene wash. In the next step of catalyst preparation, a phenol of choice is reacted with the aluminum which has been singly or doubly bonded to the resin so as to replace one or both, usually both of the pendant ethyl (more generally alkyl) groups still attached to the aluminum. Where only one or two pendant ethyl groups remains on the aluminum which has been twice bonded to the resin, then only one or two additional moles of ethane are evolved when the phenol of choice is reacted with the aluminum. The above procedure provides a heterogeneous catalyst species having one, two, or three (where tetracoordination prevails) phenoxide groups attached to aluminum which is in turn bonded once or twice to the resin structure.

In other cases such as where the resin is a cross-linked polyester resin, an aluminum moiety such as triethylaluminum attacks the pendant ester group to react with the carboxylic substituent in such a fashion that one of the ethyl groups of the triethylaluminum attaches to the carbon of the pendant carboxylic group and the remaining diethylaluminum residue attaches to the carbonyl oxygen of the carboxylic ester. Thus, it is observed that no ethane is in fact evolved upon addition of triethylaluminum to cross-linked polyester resin. Following addition of the triethylaluminum or similar aluminum compound to the polyester resin, the phenol of choice such as ortho-tert-butylphenol is added to replace both ethyl groups pendant on the aluminum which has been attached to the pendant polyester group of the resin. This provides a heterogeneous catalyst having an ethyl group attached to the carbon of the pendent ester and an aluminum diphenoxide (or triphenoxide with tetracoordination) attached to the formerly double bond oxygen of the ester thereby providing an effective heterogeneous resin-bonded aluminum phenoxide catalyst.

In the preparation of the heterogeneous catalyst of the invention, a solid polymeric resin having functional groups which have a highly electronegative atom with a donateable hydrogen atom or other electropositive leaving group (to facilitate reaction with the aluminum compound) is reacted with an aluminum compound to substituted the aluminum on the resin for the donated hydrogen atom or other leaving group. The portion of the resin remaining after such a reaction is referred to as the residue of the resin and represented as "Resin-". Thus for the phenol-formaldehyde condensation resin having pendant hydroxyl groups, "Resin-" is the polymeric structure with the oxygen of the pendant hydroxyl group bonded to the aluminum. Similarly, the pendant ester group —COOR of the cross-linked polyester resins, when reacted with triethylaluminum, becomes

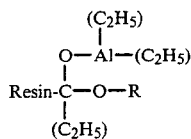

In accordance with the above, the invention also includes a resin-bonded aluminum phenoxide catalyst as described above. A preferred embodiment of the inventive catalyst is one wherein the resin is a phenol-formaldehyde condensation resin.

The heterogeneous catalyst of the invention provides a new route to ortho-alkylphenols, especially commercially valuable phenols such as 2,6-di-tert-butylphenol, ortho-sec-butylphenol, and the like. Furthermore, the heterogeneous catalyst process of the invention is well suited to a fixed bed embodiment for a continuous process when the bed is properly sized to provide the reactivity required by the reaction conditions, the phenol being alkylated, and the olefin being used. Use of the heterogeneous catalyst of the invention reduces pollution control problems by greatly reducing the amount of phenol-bearing aluminum waste encountered in homogeneous aluminum aryloxide catalyst systems thereby greatly reducing the operating costs for alkylating phenols. Use of the heterogeneous catalyst systems of the invention has resulted in very high yields suitable for commercial operation. For example, ortho-tert-butylphenol and isobutylene may be reacted to form 2,6-di-tert-butylphenol in a yield as high as 98.5%.

The heterogeneous catalysts of the invention are suitable for regeneration after use by simple toluene washing and retreating with aluminum alkyls or the like. In some embodiments it may be preferable to reduce the rate of agitation of the reaction wherein agitation is used to disperse the heterogeneous catalyst. Too high a rate of agitation may result in breakdown of the resin particles and/or destruction of the catalytic activity.

In alkylations performed using various resins, the thiol resin was found to be catalytically very active on the first run but somewhat slow in subsequent runs. The ester resin was found to have a great aluminum capacity and showed good catalytic activity for up to 5 cycles. The phenolic resin was found to have good aluminum retention capability but the catalyst life may be short in some cases.

In preparation of a heterogeneous ortho catalyst the catalyst was easily poisoned by phenol, water, and the like. Furthermore, it may be that the resin matrix itself is alkylated thereby detracting from catalytic activity. One attempt was made to prepare a heterogeneous catalyst from the phenolic resin using 2,6-di-tert-butylphenol but this attempt was not successful. The catalyst prepared from phenolic resin, triethylaluminum, and 2,4-di-tert-butylphenol were active but somewhat slower and less selective for alkylation.

According to the process of the invention, the aluminum compound may be added to the resin for reaction therewith over a broad range of temperatures so long as the attachment of the aluminum to the resin without destruction of the resin is accomplished. A suitable range of temperatures for this addition is $-20°$ C. to about $75°$ C. preferably $-20°$ C. to about $35°$ C. Conveniently, the aluminum or aluminum compound is added at about room temperature. This is especially facile for aluminum alkyl compounds which readily react with the resins to attach aluminum thereto.

The phenoxide-donating phenol may be added to the aluminum-bearing resin over a broad range of temperatures as well so long as formation of the resin-bonded aluminum phenoxide heterogeneous catalyst is accomplished. For formulation of the heterogeneous "ortho" catalyst, the ortho-alkylphenol is preferably added at the minimum temperature possible while still forming catalyst. This minimizes transalkylation of the ortho alkyl group (e.g., tert-butyl). The time of exposure of the phenol to the aluminum-bearing resin may vary depending upon the amount of phenoxide desired and the temperature used. A suitable range for formation of the phenoxide is about $-10°$ C. to $50°$ C.

If the reactive aluminum compound used to make the heterogeneous catalyst was an aluminum phenoxide, e.g. aluminum tri-(ortho-tert-butylphenoxide), the resulting catalyst will be phenoxide substituted and a donor phenol will not be needed.

The addition of the reactive aluminum compound and the phenoxide-donating phenol may be accomplished at atmospheric pressure although subatmospheric and superatmospheric pressure may also be used. Conveniently, room temperature and pressure conditions are used for formation of the catalyst with aluminum alkyls. Preferably it is conducted under an inert atmosphere, e.g. nitrogen.

The alkylation reaction of the invention may be carried out over a broad range of temperatures depending upon the heterogeneous catalyst used, the phenol to be alkylated, and the olefin used for alkylation. The temperature should be high enough to accomplish the alkylation of the phenol at a reasonable rate and low enough not to destroy the formed product, catalyst, or reactants prior to formation of the desired products. A suitable range of temperatures for the alkylation procedures in general is about −20° C. to 150° C., more preferably −20° C. to 120° C. For the embodiment using the heterogeneous ortho catalyst of the invention, a suitable range of temperatures is about −20° C. to 50° C., preferably −10° C. to 30° C.

A broad range of pressures is usable with the heterogeneously catalyzed process of the invention. The pressure should be high enough to provide adequate amounts of olefin to the phenol and catalyst mixture so as to accomplish alkylation but not so high as to interfere with obtaining the desired alkylation product or otherwise interfere with the reaction such as by degradation of reactants or product. Normally, the alkylation process is carried out in excess of 100 psig. A suitable range is 20–5,000 psig and a preferred range is 20–1,000 psig olefin pressure. When using the ortho-catalyst even lower pressures are possible dow to atmospheric.

The heterogeneous catalyst should be provided in such an amount that adequate aluminum phenoxide reaction sites are available to alkylate the phenol with the olefin. A suitable range of catalyst amount is from about 1 weight part to about 10 weight parts catalyst to 100 weight parts of phenol to be alkylated. Advantageously, an autoclave or other similar pressure vessel is sealed and used for the alkylation reaction. Conveniently, 20% excess olefin is fed normally at room temperature while the reaction mixture is constantly agitated. Thereafter, the temperature inside the reaction vessel may be controlled at the desired level.

The following non-limiting examples will illustrate the embodiments of this invention.

EXAMPLE 1

A 100 gram portion of fresh wet Rohm & Haas Duolite ® S-761 solid polymeric ion exchange resin was dried under vacuum at about 80° C. until substantially all of the absorbed water had been removed. This resulted in about 50 grams dry resin. The resin was then slurried in 200 ml. dry toluene under a nitrogen atmosphere. A stoichiometric excess (about 20–25 ml.) of triethylaluminum (TEA) was slowly added to the slurry and was allowed to react until no further ethane evolution was observed. The resin (now about 59 grams) was then subjected to five (50–200 ml.) washes with dry toluene to remove all of the unreacted TEA. This assured the presence of only heterogeneous catalyst. Liquid ortho-tert-butylphenol, 300 grams, was then slowly added to the resin/toluene mixture at room temperature (26° C.) and allowed to react until ethane evolution ceased. The stoichiometric amount of phenol needed can be determined from the amount of aluminum taken up on the resin and the single or double functionality of the aluminum. The weight ratio of ortho-tert-butylphenol to resin was about 6:1. The ortho-tert-butylphenol/catalyst mixture was charged to an autoclave and sealed. Twenty percent excess of the amount required to make 2,6-di-tert-butylphenol of isobutylene (about 125 grams) was fed at room temperature (27°–32° C.) with constant agitation of the reaction mixture. Initial reaction pressure was 60 psig, partially (about 15 psig) due to the nitrogen blanket over the mixture prior to isobutylene feed. The reaction vessel temperature was controlled at about 32° C. throughout the reaction. After 1 hour and 45 minutes the reaction mass contained 91% 2,6-di-tert-butylphenol. The heterogeneous catalyst was readily separated by decant. When a portion of the catalyst remains suspended as small particles (due to resin bead breakage from agitation or other breakdown of the resin) additional catalyst material can be readily recovered by simple filtration. Although the melting point of product 2,6-di-tert-butylphenol is 36° C., the product mixture remains liquid since small portions of reactant and by-product phenols strongly depress the melting point below most ambient temperatures. Thus only the catalyst falls out of the reaction mixture. The liquid of the reaction mass was decanted and subsequent reactions were carried out using the same solid heterogeneous catalyst. The reaction rates decreased with each successive cycle but 4 such cycles had reasonable rates to achieve significant amounts of 2,6-di-tert-butylphenol before catalyst regeneration was necessary.

Example 1 is represented in the Table below as Run 15.

EXAMPLE 2

Rohm & Haas XAD-8 solid polymeric resin, 100 grams, having an ester functionality was dried under vacuum at 80° C. until substantially all absorbed water had been removed leaving about 90 grams dry resin. The resin was slurried in 200 ml. dry toluene under a nitrogen atmosphere and excess (20-25 ml.) TEA was slowly added to the slurry at room temperature. No ethane evolution was observed. The resin was then washed five times with 200 ml. portions dry toluene to remove any excess unreacted TEA. Ortho-tert-butylphenol, 300 grams, was then slowly added to the resin/toluene mixture and allowed to react until ethane evolution ceased. The weight ratio of ortho-tert-butylphenol to catalyst was again about 7:1. The ortho-tert-butylphenol/catalyst mixture was charged to a pressure reactor vessel and sealed. Twenty percent excess isobutylene (145 grams) was fed at room temperature over 42 minutes with constant agitation. The reaction temperature was controlled at about 14°–16° C. throughout the entire reaction. Initial reaction pressure was about 35–40 psig and a maximum pressure of 57 psig was reached. The final composition contained about 76% 2,6-di-tert-butylphenol. Similar runs with the same materials and under the same conditions resulted in yields of about 87–88% and the time for the runs ranged from about 3 hours, 20 minutes to 4 hours, 10 minutes. This example and the similar runs are represented in the Table below as Runs 30–32.

A series of experiments was carried out to demonstrate the applicability of the heterogeneous catalyst of the invention. The materials, operating conditions, and results of those experiments demonstrating the use of the heterogeneous alkylation catalyst of the invention are summarized in the Table below. In each case, the resin was reacted first with triethylaluminum, the most readily available and facile aluminum alkyl, and then with ortho-tert-butylphenol. Isobutylene was the reactant olefin in each case. In some cases freshly prepared catalyst was used whereas in other cases the catalyst was recycled for a subsequent experiment as indicated.

TABLE

| RUN NO. | RESIN TYPE | TIME (HRS.) | TEMP. °C. | PRODUCT ANALYSIS* | | | | | |
|---|---|---|---|---|---|---|---|---|---|
| | | | | OTBP | 2,6-DTBP | 2,4-DTDP | 2,4,6- | DIMER | 2TBP-BE | PTBP |
| 1 | Thiol | 17.00 | 29–51 | 7.0 | 88.0 | — | 4.2 | — | 0.8 | — |

TABLE-continued

| RUN NO. | RESIN TYPE | TIME (HRS.) | TEMP. °C. | PRODUCT ANALYSIS* | | | | | | |
|---|---|---|---|---|---|---|---|---|---|---|
| | | | | OTBP | 2,6-DTBP | 2,4-DTDP | 2,4,6- | DIMER | 2TBP-BE | PTBP |
| 2 | Thiol (recycle) | 18.00 | 28–32 | 97.8 | 1.3 | — | — | — | 0.9 | — |
| 3 | Phenolic | 9.00 | 28–93 | 58.6 | 17.6 | 17.8 | 3.0 | 1.0 | 1.3 | — |
| 4 | Mixed Amine | 6.50 | 28–71 | 95.7 | 2.3 | 0.5 | 0.2 | — | 0.9 | 0.5 |
| 5 | Thiol (fresh) | 8.17 | 27–37 | 16.6 | 74.6 | 1.1 | 6.3 | 0.4 | 0.4 | 0.6 |
| 6 | Thiol (recycle) | 23.00 | 23–38 | 33.4 | 61.1 | 0.9 | 3.4 | 0.3 | 0.7 | 0.3 |
| 7 | Phenolic (fresh) | 2.33 | 19–39 | 3.8 | 84.5 | 0.3 | 9.5 | 1.0 | 0.2 | 0.3 |
| 8 | Phenolic (recycle A) | 20.50 | 25–44 | 1.9 | 90.0 | 0.2 | 6.8 | 0.3 | 0.5 | 0.2 |
| 9 | Phenolic (recycle B) | 22.50 | 24–42 | 7.9 | 85.7 | — | 5.8 | — | 0.7 | — |
| 10 | Phenolic (recycle C) | 48.00 | 22–36 | 5.4 | 86.5 | 0.4 | 6.3 | 0.4 | 0.7 | 0.3 |
| 11 | Phenolic (fresh) | 14.00 | 27–43 | 0.9 | 89.9 | — | 8.2 | 0.5 | 0.6 | — |
| 12 | Phenolic (recycle A) | 23.25 | 27–46 | 15.3 | 77.7 | 0.6 | 5.0 | 0.4 | 0.7 | 0.2 |
| 13 | Phenolic (recycle B) | 74.00 | 22–41 | 64.3 | 28.5 | 0.6 | 1.4 | 0.1 | 0.9 | 0.1 |
| 14 | Phenolic (recycle C) | 0.33 | 37–39 | 96.0 | 3.0 | 0.1 | 0.1 | — | 0.8 | — |
| 15 | Phenolic (fresh) | 1.30 | 19–33 | 1.6 | 90.8 | — | 6.8 | 0.3 | 0.5 | 0.5 |
| 16 | Phenolic (recycle A) | 23.42 | 23–38 | 22.5 | 63.5 | 7.1 | 4.2 | 0.2 | — | 1.8 |
| 17 | Phenolic (recycle B) | 4.92 | 24–29 | 78.4 | 19.5 | 0.4 | 1.5 | — | 0.2 | — |
| 18 | Phenolic (fresh) | 43.00 | −9 +27 | 2.3 | 90.1 | — | 7.6 | — | — | — |
| 19 | Phenolic (recycle) | 28.25 | 13–33 | 86.5 | 11.8 | .2 | 1.0 | .1 | 0.2 | 0.1 |
| 20 | Phenolic | | | ABORTED DUE TO WET RESIN | | | | | | |
| 21 | Phenolic (fresh) | 3.08 | 26–35 | 5.0 | 84.3 | 0.3 | 9.1 | 0.6 | 0.2 | 0.2 |
| 22 | Phenolic (recycle A) | 25.90 | 24–44 | 14.4 | 75.6 | 0.9 | 8.0 | 0.6 | 0.2 | 0.2 |
| 23 | Phenolic (recycle B) | | | NO REACTION OBSERVED | | | | | | |
| 24 | Acrylic Ester (fresh) | 2.20 | 29–31 | 10.7 | 75.6 | 2.7 | 9.5 | 0.6 | — | — |
| 25 | Acrylic Ester (recycle A) | 1.60 | 28–32 | 1.7 | 87.3 | 0.2 | 10.1 | 0.4 | — | — |
| 26 | Acrylic Ester) (recycle B) | 3.90 | 27–33 | 2.2 | 89.4 | — | 7.6 | 0.4 | — | — |
| 27 | Acrylic Ester (recycle C) | 5.25 | 24–33 | 8.1 | 85.1 | 0.3 | 5.6 | 0.5 | — | — |
| 28 | Acrylic Ester (recycle D) | 7.00 | 28–32 | 22.2 | 72.7 | 0.6 | 3.7 | 0.3 | — | — |
| 29 | Acrylic Ester (recycle E) | 7.60 | 33–43 | 57.7 | 48.7 | 1.3 | 2.1 | 0.3 | — | — |
| 30 | Acrylic Ester (fresh) | 3.67 | 14–16 | 15.6 | 75.8 | 1.4 | 6.4 | 0.3 | 0.2 | — |
| 31 | Acrylic Ester (recycle A) | 3.75 | 13–16 | 4.8 | 88.0 | 0.2 | 5.9 | 0.3 | 0.2 | 0.3 |
| 32 | Acrylic Ester (recycle B) | 4.17 | 15–16 | 8.0 | 87.1 | 0.2 | 3.9 | 0.3 | 0.3 | 0.2 |
| 33 | Acrylic Ester (recycle C) | 22.37 | 14–17 | 35.3 | 60.1 | 0.8 | 2.1 | 0.2 | 0.4 | 0.2 |
| 34 | Carboxylic Acid | | | NO REACTION OBSERVED | | | | | | |
| 35 | Phenolic | | | NO REACTION OBSERVED | | | | | | |
| 36 | Phenolic | 1.75 | 25–38 | 1.0 | 90.9 | 0.1 | 6.9 | 0.5 | 0.3 | 0.2 |
| 37 | Phenolic (recycle) | 3.58 | 23–34 | 4.6 | 87.6 | 0.3 | 6.4 | 0.5 | 0.4 | 0.2 |
| 38 | Phenolic | 5.37 | 32 | 6.9 | 83.5 | 0.5 | 6.3 | 0.4 | 0.3 | 0.1 |

Product analysis is by weight percent exclusive of light ends. OTBP is ortho-tert-butylphenol; 2,6-DTBP is 2,6-di-tert-butylphenol; 2,4-DTDP is 2,4-di-tert-butylphenol; 2,4,6- is 2,4,6-tri-tert-butylphenol; DIMER is 1,1,3,3-tetramethyl-butylphenol; PTBP is para-tert-butylphenol; 2TBP-BE is 2-tert-butylphenyl butyl ether.

The relatively slow reaction rates in experiments 1–7 were attributed to poor catalyst preparation. In Run No. 7 the thermocouple was accidentally left out of the thermal well resulting in somewhat higher temperature during the first portion of the alkylation. This did not seem to seriously affect the alkylation. In Run No 11 the ortho-tert-butylphenol was first dried with a molecular sieve to lower the water level and increase the ortho directing effect of the heterogeneous ortho catalyst. The drying reduced the water level of the OTBP from 0.05% by weight to 0.013% by weight. In Run No. 12 an additional portion of isobutylene was charged after 20 hours of reaction and warmed somewhat for the continued reaction. The recycled phenolic resin heterogeneous catalyst of Run No. 14 was washed with 350 ml of toluene at 150° F. for 20 to 30 minutes but this did not seem to improve its activity.

In Runs 15–17 toluene was used as a diluent to cleanse the resin. In Run 16 the dipleg became plugged and the reaction vessel was opened to obtain the sample but some isobutylene was lost. The isobutylene was recharged but at too low a level thereby decreasing the production of the desired 2,6-di-tert-butylphenol. Runs 15–17 were diluted with 24% by weight toluene whereas Run 18 was diluted with 75 ml of toluene in a reaction which contained 300 grams ortho-tert-butylphenol. In Run 18 the temperature was only briefly at 27° C. and primarily at about 16° C. In Run No. 19 there was no apparent reaction for reasons unknown. Run No. 20 was aborted because the resin was not well dried prior to preparation of the heterogeneous catalyst.

Run 21 was diluted with methylene chloride and some additional isobutylene was added after about 2 hours and 20 minutes. This assured complete reaction of the olefin with the ortho-tert-butylphenol. Run 22 was carried out using 50 ml methylene chloride diluent and with a 30% stoichiometric excess of isobutylene.

The prepared heterogeneous catalyst of Run 23 was refluxed in methylene chloride for 1 and ½ hours before charging and the reaction mixture did not react after 19 hours. In Run No. 28 the reactor was vented after discovering that nitrogen rather than isobutylene was being charged. Thereafter, isobutylene was charged and the reaction proceeded as usual.

In Runs 24–29, it was calculated that approximately 4.55 grams of aluminum were reacted onto the resin and remained there after toluene washes.

In Run No. 30 the isobutylene feed was completed after 48 minutes. Aluminum analysis of the decanted liquid, centrifuged liquid, and solids layer revealed that about 59.3% of the aluminum charged to the resin was lost after the reaction. In Run No. 31 the isobutylene feed was completed in about 5 minutes and only about 11.2% of the aluminum charged to the resin had been lost after the reaction. Similarly, in Run 32 only about 3.1% was lost and in Run 33 about 6.8% was lost.

In Run No. 24 in the Table, the product solution was decanted and found to contain 0.60 weight percent aluminum. The decant was filtered leaving 0.45 weight percent aluminum. The filtered 0.15 weight percent aluminum (in the form of aluminum compounds and resin-aluminum catalyst materials) was put back into the reactor for subsequent runs. In the next run, a recycle, the amount of aluminum lost was 0.09 weight percent (after filtration) while the catalyst activity remained excellent. In the next four recycle runs the catalyst activity remained excellent to good and there was no loss of aluminum in any of the four runs. The resin used was Rohm & Haas XAD-8 acrylic ester resin.

Similarly in Runs No. 30 through No. 33 in the Table, the total loss of aluminum was 80.4 percent of the aluminum reacted onto the catalyst before Run No. 30. Yet the reactivity remained high as seen in the Table (75.8% to 88.0% to 87.1% to 60.1% product 2,6-). Compare the loss of four quantities of aluminum loss for four successive homogeneous catalyst runs. Thus for this sequence of reactions alone the aluminum loss is only about one-fifth that lost in homogeneous runs—and the catalyst still has good activity.

The savings in aluminum is more than the simple cost of aluminum alone. The savings in reduced disposal cost is more significant than the cost of the metal.

In the homogeneously catalyzed process, the aluminum is acidified with sulfuric acid to make aluminum sulfate which is soluble in the acid phase. The acid phase with aluminum sulfate is cut from the mixture and treated with caustic to form aluminum hydroxide. This greatly increases the weight of the waste material but allows disposal thereof. This neutralized solution is mechanically dewatered somewhat and sent to landfill where it must be closely monitored. The acid/base treatment of the homogeneous catalyst prevents loss of product which is somewhat soluble in basic aqueous solutions.

Thus a significant decrease in the loss of aluminum per batch run (or in a fixed bed) represents a great savings in disposal handling and cost.

In Runs 34 and 35 no reaction was observed and this was attributed to a bad resin batch. In Run 36 a fresh batch of resin was used and the highest aluminum absorption rate of the series was achieved with only 5% loss of aluminum from the resin after the reaction. The mole ratio of ortho-tert-butylphenol to dissolved aluminum in Runs 36–38 was 182, 282, and 635 respectively. Only 2.9% of the aluminum was lost in Run 37 and only 1.4% was lost in Run 38. It should be noted that Runs 36–38 were a series of runs using the same catalyst (recycled to Runs 37 and 38). Thus, the total loss of aluminum from these three runs was only 9.3%. This should be compared with the massive loss of phenol-bearing aluminum which must be disposed of as a waste stream in a homogeneously catalyzed process.

In another experiment not listed above, phenol and isobutylene were reacted in the presence of a heterogeneous catalyst formed from Rohm & Haas Duolite ® S-761 phenol-formaldehyde resin and phenol ($C_6H_5OH$). The yield at about 95° C. was about 9.0% 2,6-di-tert-butylphenol.

It should be apparent to the skilled artisan that the invention may be varied considerably in its practice without departing from its lawful scope and true spirit as defined by the appended claims.

We claim:

1. A process for alkylating phenols comprising reacting in a liquid reaction medium a mixture of:
   (a) a phenol having at least one ortho or para position unsubstituted except for H;
   (b) an olefin; and
   (c) a heterogeneous catalyst comprising an aluminum phenoxide bonded to a solid polymeric resin.

2. The process of claim 1 wherein said medium is a phenol.

3. The process of claim 1 wherein said medium is an innocuous hydrocarbon.

4. The process of claim 3 wherein said hydrocarbon is toluene.

5. The process of claim 1 wherein said phenol has the structure I:

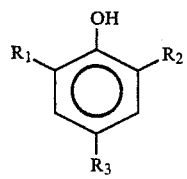

(I)

wherein $R_1$, $R_2$, and $R_3$ are independently selected from the group consisting of H, alkyl of from 1–12 carbon atoms, cycloalkyl of from 5–12 carbon atoms, and aralkyl of from 7–12 carbon atoms wherein at least one of $R_1$, $R_2$, and $R_3$ is H.

6. The process of claim 5 wherein said phenol is the compound phenol, $C_6H_5OH$.

7. The process of claim 5 wherein $R_2$ is H, $R_3$ is H, and $R_1$ is alkyl of from 1 to 12 carbon atoms.

8. The process of claim 7 wherein $R_1$ is a sec-alkyl or tert-alkyl.

9. The process of claim 8 wherein $R_1$ is sec-butyl or isopropyl.

10. The process of claim 8 wherein $R_1$ is tert-butyl.

11. The process of claim 7 wherein $R_1$ is methyl.

12. The process of claim 1 wherein said heterogeneous catalyst is the reaction product formed by (a) reacting an aluminum alkyl with a solid polymeric resin to bond the aluminum of said aluminum alkyl to said resin, followed by (b) reaction with a phenol having at least one ortho or para position unsubstituted except for H.

13. The process of claim 1 wherein said aluminum phenoxide is a phenoxide of a phenolic compound having the structure:

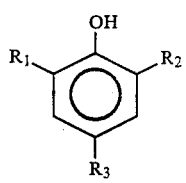

wherein $R_1$, $R_2$, and $R_3$ are independently selected from the group consisting of H, alkyl of from 1–12 carbon atoms, cycloalkyl of from 5 to 12 carbon atoms, and aralkyl of from 7-12 carbon atoms.

14. The process of claim 13 wherein said phenolic compound is the compound phenol, $C_6H_5OH$.

15. The process of claim 13 wherein $R_2$ is H, $R_3$ is H, and $R_1$ is alkyl of 1 to 12 carbon atoms.

16. The process of claim 15 wherein $R_1$ is methyl.

17. The process of claim 15 wherein $R_1$ is sec-alkyl or tert-alkyl.

18. The process of claim 17 wherein $R_1$ is sec-butyl or isopropyl.

19. The process of claim 17 wherein $R_1$ is tert-butyl.

20. The process of claim 13 wherein $R_1$ is alkyl, $R_2$ is alkyl, and $R_3$ is H.

21. The process of claim 1 wherein said solid polymeric resin is a phenol-formaldehyde condensation resin.

22. The process of claim 1 wherein said solid polymeric resin is a cross-linked acrylic polyester resin.

23. The process of claim 1 carried out at about $-20°$ C. to 120° C.

24. The process of claim 1 carried out at about 20-5000 psig.

25. The process of claim 1 further comprising, after the alkylation reaction, separating the heterogeneous catalyst.

26. The process of claim 25 wherein said separating comprises decanting the liquid of the reaction mixture from the settled heterogeneous catalyst.

27. The process of claim 26 wherein said separating further comprises filtering the liquid decant to recover additional heterogeneous catalyst.

28. The process of claim 25 further comprising carrying out a subsequent alkylation of a phenol with an olefin and the recovered heterogeneous catalyst.

29. A process for preparing di-ortho-substituted phenol comprising reacting a mixture consisting essentially of:

(a) a phenol having the formula:

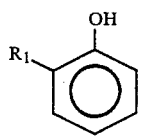

wherein $R_1$ is selected from the group consisting of alkyl of from 1-12 carbon atoms, cycloalkyl of from 5-12 carbon atoms and aralkyl of from 7-12 carbon atoms and (b) an olefin (c) in contact with heterogeneous catalyst comprising an aluminum phenoxide of a phenol having the formula:

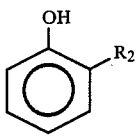

wherein $R_2$ is selected from the group consisting of alkyl of from 1-12 carbon atoms, cycloalkyl of from 5-12 carbon atoms, and aralkyl of from 8-12 carbon atoms, said aluminum phenoxide being bonded through aluminum to a solid polymeric resin, said mixture being substantially free of phenol and phenol-generating ethers.

30. The process of claim 29 wherein $R_1$ is the same as $R_2$ and said olefin corresponds to $R_1$.

31. The process of claim 30 wherein $R_1$ and $R_2$ are tert-butyl and said olefin is isobutylene.

32. The process of claim 29 carried out at about $-20°$ C. to 50° C.

33. The process of claim 29 carried out at carried out at about 20-5000 psig.

34. A two stage process for producing di-ortho-substituted phenol comprising:

(a) reacting an olefin and the compound phenol in the presence of an aluminum-containing catalyst to form mono-ortho-substituted phenol intermediate; and (b) in the absence of phenol and phenol-generating ethers, reacting said mono-ortho-substituted phenol intermediate and an olefin in the presence of a heterogeneous catalyst comprising an aluminum phenoxide of an ortho-substituted phenolic compound, said aluminum phenoxide being bonded through aluminum to a solid polymeric resin, thereby producing said di-ortho-substituted phenol and minimizing the formation of tri-substituted phenol.

35. The two stage process of claim 34 wherein stage (b) is carried out with said heterogeneous catalyst in a fixed bed.

36. The two stage process of claim 34 wherein the olefin in both stages is isobutylene so as to form 2,6-di-tert-butylphenol product.

37. The two stage process of claim 34 wherein the absence of phenol and phenol-generating ethers in stage (b) is accomplished by (i) reacting all the starting phenol to said di-ortho-substituted phenol and said intermediate or (ii) adding aluminum or a reactive aluminum compound sufficient to react with all unreacted phenol to form aluminum tris phenoxide.

38. The two stage process of claim 34 wherein said aluminum-containing catalyst of stage (a) is gamma alumina.

39. The two stage process of claim 34 wherein the olefin in both stages is butene-1 or butene-2 so as to form di-ortho-sec-butylphenol.

40. The two stage process of claim 34 wherein the olefin in both stages is propylene so as to form di-ortho-isopropylphenol.

41. The process of claim 34 wherein stage (b) is carried out at about $-20°$ C. to 50° C. and 20-5000 psig.

* * * * *